(12) United States Patent
Pinkos et al.

(10) Patent No.: US 7,754,925 B2
(45) Date of Patent: Jul. 13, 2010

(54) METHOD FOR THE HYDROGENATION OF MASS FLUXES CONTAINING ALDEHYDE

(75) Inventors: Rolf Pinkos, Bad Duerkheim (DE); Gerd-Dieter Tebben, Goettingen (DE); Alexander Hauk, Ludwigshafen (DE); Christian Mueller, Mannheim (DE); Harald Rust, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/995,518

(22) PCT Filed: Jul. 11, 2006

(86) PCT No.: PCT/EP2006/064115

§ 371 (c)(1),
(2), (4) Date: Jan. 11, 2008

(87) PCT Pub. No.: WO2007/006789

PCT Pub. Date: Jan. 18, 2007

(65) Prior Publication Data

US 2008/0221366 A1    Sep. 11, 2008

(30) Foreign Application Priority Data

Jul. 12, 2005   (DE) ...................... 10 2005 032 541

(51) Int. Cl.
*C07C 45/00* (2006.01)
(52) U.S. Cl. .................. 568/343; 568/350; 568/458; 568/881
(58) Field of Classification Search ............ 568/458, 568/881, 343, 358
See application file for complete search history.

(56) References Cited

U.S. PATENT DOCUMENTS

| 316,917 A | 4/1885 | Russell |
|---|---|---|
| 3,804,914 A | 4/1974 | Fahey |
| 4,213,000 A | 7/1980 | Coates |
| 4,960,960 A | 10/1990 | Harrison et al. |
| 5,128,296 A | 7/1992 | Matson et al. |
| 5,177,278 A | 1/1993 | Sanchez |
| 5,180,870 A | 1/1993 | Paciello |
| 5,210,349 A | 5/1993 | Matson et al. |
| 5,321,176 A | 6/1994 | Sanchez |
| 6,723,883 B1 | 4/2004 | Therre et al. |
| 2006/0281952 A1 | 12/2006 | Teles et al. |

FOREIGN PATENT DOCUMENTS

| DE | 25 19 817-OS | 11/1976 |
|---|---|---|
| DE | 103 44 595 A1 | 5/2005 |
| EP | 0 133 739 B1 | 3/1985 |
| EP | 0 285 420 A1 | 10/1988 |
| EP | 1 477 219 A1 | 11/2004 |
| GB | 1 519 677 | 8/1978 |
| GB | 1 551 741 | 8/1979 |
| WO | WO-01/27061 | 4/2001 |

OTHER PUBLICATIONS

International Preliminary Report on Patentability (Chapter 1) for International Application No. PCT/EP2006/064115 dated Jan. 29, 2008 (14 pages).
Fahey, D., "Selective Hydrogenation of 1,5,9-Cyclododecatriene to Cyclododecene Catalyzed by Ruthenium Complexes," *J. Org. Chem.*, vol. 28, No. 1, (1973), p. 80-87.
Schiffer, T. et al., "Cyclododecatriene, Cyclooctadiene, and 4-Vinylcyclohexene," *Ullmann's Encyclopedia of Industrial Chemistry*, 6th Edition, Electronic Release, Wiley VCH, (2000), p. 1-4.
Weber, H. et al., "Zur Bildungsweise von cis, trans,trans-Cyclododecatrien-(1,5,9) mittels titanhaltiger Ziegler-Katalysatoren," Liebigs Ann. Chem, 681, (1965), p. 10-20.
Weissermel, K. et al. "Industrielle Oganische Chemie," 5th Edition, Wiley VCH, (1998), p. 149-150.

*Primary Examiner*—Sikarl A Witherspoon
(74) *Attorney, Agent, or Firm*—Connolly Bove Lodge & Hutz LLP

(57) ABSTRACT

The present application relates to a process for reacting a composition I comprising at least one aldehyde with hydrogen in the presence of a catalyst in at least one main reactor and at least one postreactor, wherein at least 50% of the fresh hydrogen fed to the reaction system is fed into at least one postreactor. In a preferred embodiment, composition I comprises at least one further organic compound.

17 Claims, No Drawings

METHOD FOR THE HYDROGENATION OF MASS FLUXES CONTAINING ALDEHYDE

CROSS REFERENCE TO RELATED APPLICATIONS

This application is a National Phase filing under 35 U.S.C. §371 of PCT/EP2006/064115 filed Jul. 11, 2006, which claims priority to Patent Application No. 102005032541.6, filed in Germany on Jul. 12, 2005. The entire contents of each of the above applications are incorporated herein by reference.

The present invention relates to a process for reacting a composition I comprising at least one aldehyde with hydrogen in the presence of a catalyst in at least one main reactor and at least one postreactor, wherein at least 50% of the fresh hydrogen fed to the reaction system is fed into at least one postreactor.

Hydrogenations of aldehydic compositions are widespread. For example, in the preparation of so-called oxo alcohols, after hydroformylation of olefins to aldehydes, the latter are hydrogenated to alcohols (K. Weissermel, H. J. Arpe, "Industrielle Organische Chemie" [Industrial Organic Chemistry], 5th. Edition, 1998, pages 149-150, Wiley-VCH Verlag).

For example, lysmeral is prepared by hydrogenating dehydrolysmeral, if appropriate in the presence of tert-butylbenzaldehyde, as described in WO 01/27061.

Likewise known are processes in which an organic compound which comprises an aldehyde as an impurity is hydrogenated. An example is the hydrogenation of cyclododecadienone to cyclododecanone, in which small amounts of aldehydes may be present in the cyclododecadienone. Such a process is described, for example, in DE 103 44 595 A.

In the hydrogenation of butynediol to butanediol, it is equally possible for small amounts of formaldehyde to be present from the synthesis of the butynediol from formaldehyde and acetylene. However, it is also possible to deliberately add formaldehyde in order to obtain alkylated butanediol, as disclosed, for example, in EP 0 133 739 B1.

In these hydrogenation processes, decomposition of aldehydes present in the reaction system leads to the formation of CO, which is known to be capable of hindering the hydrogenation. This a problem especially when full conversion of the reactants is required, for example in order to obtain products in high purity or to avoid complicated separation processes. The problem is often confronted by hydrogenating at very high pressures in order to convert CO which forms substantially fully to methane. However, the high pressure required leads to the occurrence of high investment and operating costs for the process.

In order to achieve a maximum conversion, it is generally customary to hydrogenate in two steps, a so-called main reactor and at least one postreactor. The greater part of the heat of hydrogenation is released in the main reactor and removed by external circulation. The fresh hydrogen is typically introduced at least for the most part into the main reactor and the offgas is discharged from or downstream of the last postreactor.

In such a process, high CO concentrations are present, especially in the postreactor, and full conversion is not achieved under some circumstances. Thus, products are obtained which comprise secondary components which in some cases can be removed only by complicated and costly purification steps.

Accordingly, it was an object of the present invention to provide a process for hydrogenating aldehydic compositions to obtain a maximum conversion of the reactants.

It was a further object of the present invention to provide a process for hydrogenating aldehydic compositions in which products are obtained in high purity.

It was a further object of the present invention to provide an inexpensive process for hydrogenating aldehydic compositions in which products are obtained in high purity.

According to the invention, this object is achieved by a process for reacting a composition I comprising at least one aldehyde with hydrogen in the presence of a catalyst in at least one main reactor and at least one postreactor, wherein at least 50% of the fresh hydrogen fed to the reaction system is fed into at least one postreactor.

In a preferred embodiment, the present invention relates to a process as described above for reacting a composition I comprising at least one aldehyde with hydrogen in the presence of a catalyst in at least one main reactor and at least one postreactor, wherein more than 50% of the hydrogen used in at least one main reactor stems from the offgas of the postreactor.

In the context of the present invention, "fresh hydrogen" is understood to mean hydrogen or a hydrogen containing mixture which is fed to the reaction system.

In the context of the present application, the term "reaction system" is understood to mean the totality of the reactors utilized for the process according to the invention, i.e. at least one main reactor and at least one postreactor.

It has been found that it is particularly advantageous when the hydrogen added to the reaction system, at least for the most part, is introduced into the postreactor and is transferred from there into the main reactor as offgas of the postreactor. According, to the invention, the greater part of the offgas is discharged from or downstream of the main reactor. According to the invention, preferably only the hydrogen dissolved in the product stream of the main reactor passes from the main reactor into the postreactor.

One advantage of the process according to the invention is that a low CO concentration is present in the postreactor. This measure succeeds in maximizing the conversion without having to resort to high pressures. Thus, it is impossible in the process according to the invention to save catalyst and reactor space. A further advantage is the increased lifetime of the catalysts, especially in the postreactor(s).

In general, hydrogenations in which full conversion is desired are effected with hydrogen excess. The process according to the invention is notable in that the hydrogen excess, which inevitably has to be disposed of and thus causes costs, can be relatively small. The hydrogen excess (mol % of hydrogen based on the stoichiometrically required hydrogen) is preferably between 0.1 and 50 mol %, more preferably between 0.3 and 40 mol %, most preferably between 0.5 and 25 mol %.

In a preferred embodiment, the present invention therefore also relates to a process as described above, wherein hydrogen is used in an excess of from 0.1 to 50 mol %. The process according to the invention can be employed for the reaction of a composition I comprising at least one aldehyde. In a preferred embodiment, composition I may, in addition to the aldehyde, also comprise at least one further organic compound which is hydrogenated in the process according to the invention. In the context of the present invention, the organic compound is thus a hydrogenatable organic compound.

The present invention accordingly also relates to a process as described above for reacting a composition. I comprising at least one aldehyde with hydrogen in the presence of a catalyst in at least one main reactor and at least one postreactor, wherein composition I comprises at least one further organic compound.

When the aldehyde is the main component of composition I to be hydrogenated, the aldehyde content in the context of the present invention is preferably at least 80% and at most 100%, more preferably at least 90% and at most 99.9%, more preferably at least 95%, most preferably at least 98% and at most 99.5%.

When aldehydes are present as secondary components, composition I in the context of the present invention comprises in particular from 20 to 99.9% by weight, based on composition 1, of a further organic, compound. Composition I comprises preferably from 70 to 98% by weight, more preferably from 90 to 95% by weight, of a further organic compound.

In addition to organic constituents, composition I may also comprise inorganic compounds, for example Water.

In the context of the present invention, the organic compounds used may be all suitable compounds which can be hydrogenated with hydrogen in the presence of a catalyst. Suitable in accordance with the invention are, for example, unsaturated, optionally substituted compounds such as alkenes or alkynes, aromatic compounds, ketones, esters, acids, anhydrides, amides, nitrites or nitro compounds.

According to the invention, it is possible in particular to use organic compounds which comprise aldehydes, for example as a result of the preparation process. Such compounds are, for example, cyclododecadienone, dehydrolysmeral or 1,4-butynediol.

Accordingly, the present invention relates, in a further embodiment, to a process as described above for reacting a composition I, comprising at least one aldehyde and at least one further organic compound with hydrogen in the presence of a catalyst in at least one main reactor and at least one postreactor, wherein the organic compound is selected from the group consisting of cyclododecadienone, dehydrolysmeral or 1,4-butynediol.

In a preferred embodiment of the present invention, composition I may comprise, as the organic compound, cyclododecadienone which has been obtained by reacting a cyclododecatriene with dinitrogen monoxide.

In this case, at least one suitable solvent or diluent may be used for the reaction of the cyclododecatriene with dinitrogen monoxide. These include cyclododecane or cyclododecanone or saturated aliphatic or aromatic, optionally alkyl-substituted hydrocarbons, substantially all common solvents and/or diluents being suitable with the proviso that they have neither a C—C double bond nor a C—C triple bond nor an aldehyde group.

In general, there is no need to add a solvent or diluent in the reaction of cyclododecatriene with dinitrogen monoxide.

The temperatures in the reaction of cyclododecatriene with dinitrogen monoxide are preferably in the range from 140 to 350° C., more preferably in the range from 180 to 320° C. and particularly preferably in the range from 200 to 300° C.

It is possible to carry out the reaction of cyclododecatriene with dinitrogen monoxide at two or more temperatures or in two or more temperature ranges, each of which is within the above-specified limits. Temperature changes in the course of the reaction can be performed continuously or else discontinuously.

The pressures in the reaction of cyclododecatriene with dinitrogen monoxide are preferably higher than the autogenous pressure of the reactant or product mixture at the selected reaction temperature or the selected reaction temperatures. The pressures are preferably in the range from 1 to 1000 bar, more preferably in the range from 40 to 300 bar and particularly preferably in the range from 5.0 to 200 bar.

It is possible to carry out the reaction of cyclododecatriene with dinitrogen monoxide at two or more pressures or in two or more pressure ranges, each of which is within the above-specified limits. Pressure changes in the course of the reaction can be performed continuously or else discontinuously.

With regard to the reactors usable for the reaction of cyclododecatriene with dinitrogen monoxide, there are no particular restrictions. In particular, the reaction can be effected in batchwise mode or in continuous mode. Accordingly, the reactors used may, for example, be at least one CSTR (Continuous Stirred Tank Reactor) with at least one internal and/or at least one external heat exchanger, at least one tubular reactor or at least one loop reactor. It is equally possible to configure at least one of these reactors in such a way that it has at least two different zones. Such zones may differ, for example, in reaction conditions, for example the temperature or the pressure and/or in the geometry of the zone, for example the volume or the cross section. When the reaction is carried out in two or more reactors, it is possible to use two or more identical reactor types or at least two different reactor types.

Preference is given to carrying out the reaction of cyclododecatriene with dinitrogen monoxide in a single reactor. For example, preference is given to the reaction in continuous mode.

The residence time of the reactant in the at least one reactor in the reaction of cyclododecatriene with dinitrogen monoxide is generally in the range of up to 20 h, preferably in the range from 0.1 to 20 hours, more preferably in the range from 0.2 to 15 hours and particularly preferably in the range from 0.25 to 10 h.

In the feed which is fed to the reaction of dinitrogen monoxide with cyclododecatriene, the molar ratio of dinitrogen monoxide to cyclododecatriene is generally in the range from 0.05 to 4, preferably in the range from 0.06 to 1, more preferably in the range from 0.07 to 0.5 and particularly preferably in the range from 0.1 to 0.4.

The reaction of cyclododecatriene with dinitrogen monoxide may be carried out in such a way that, at a very high selectivity for cyclododecadienone, a conversion of cyclododecatriene in the range of up to 50%, preferably in the range from 5 to 30% and especially preferably in the range from 10 to 20% is achieved. The selectivity based on cyclododecadienone is generally at least 90%, preferably at least 92.5% and more preferably at least 95%.

In principle, it is possible to react any cyclododecatriene or any mixture of two or more different cyclododecatrienes with dinitrogen monoxide. Examples include 1,5,9-cyclododecatrienes; for example cis,trans,trans-1,5,9-cyclododecatriene or cis,cis,trans-1,5,9-cyclododecatriene or all-trans-1,5,9-cyclododecatriene.

The cyclododecatriene used is preferably cis,trans,trans-1,5,9-cyclododecatriene.

In general, the reaction of cis,trans,trans-1,5,9-cyclododecatriene with dinitrogen monoxide results in a cyclododeca-4,8-dienone isomer mixture which comprises at least two of the isomers cis,trans-cyclododeca-4,8-dienone, trans,cis-cyclododeca-4,8-dienone and trans,trans-cyclododeca-4,8-dienone. An example of a typical isomer mixture accordingly has the isomers in a molar ratio of about 1:1:0.08. This isomer mixture may be present in the composition I used in the process according to the invention.

The reaction of cyclododecatriene with dinitrogen monoxide can in principle be effected in the presence of a catalyst, but also without addition of a catalyst.

1,5,9-cyclododecatriene can be prepared, for example, by trimerizing pure 1,3-butadiene, as described, for example, in T. Schiffer, G. Oenbrink, "Cyclodo-decatriene, cyclooctadiene and 4-vinylcyclohexane", Ullmann's Encyclopedia of Industrial Chemistry, 6th Edition (2000), Electronic Release, Wiley VCH. This process forms, in the trimerization in the presence of Ziegler catalysts for example, cis,trans,trans-1,5,9-cyclododecatriene, cis,cis,trans-1,5,9-cyclododecatriene and all-trans-1,5,9-cyclododecatriene, as described, for example, in H. Weber et al. "Zur Bildungsweise von cis,trans,trans-Cyclododecatrien-(1.5.9) mittels titanhaltiger Katalysatoren" in: Liebigs Ann. Chem. 681 (1965) p. 10-20. Cyclododecatriene can be prepared by trimerizing 1,3-butadiene using a titanium catalyst.

While all suitable titanium catalysts can in principle be used for trimerization, the titanium tetrachloride/ethylaluminum sesquichloride catalyst described in the article by Weber et al. is particularly suitable.

The butadiene used for the trimerization especially preferably has a purity determined by gas chromatography of at least 99.6% and more preferably of at least 99.65%. Especially preferably, the 1,3-butadiene used does not comprise any 1,2-butadiene nor any 2-butyne within the precision of detection.

This trimerization generally affords mixtures which comprise, at least 95% by weight, preferably at least 96% by weight and more preferably at least 97% by weight of cis, trans,trans-1,5,9-cyclododecatriene. For example, the mixtures especially preferably comprise about 98% by weight of cis,trans,trans-1,5,9-cyclo-dodecatriene.

This mixture comprising cis,trans,trans-1,5,9-cyclododecatriene may be used as such for the reaction with dinitrogen monoxide. It is equally possible to remove the cis,trans,trans-1,5,9-cyclododecatriene from the mixture by means of at least one suitable method, for example preferably by means of at least one distillation, and to use it in the reaction with dinitrogen monoxide.

According to the invention, composition I comprises an aldehyde. The process according to the invention may in principle be carried out in the presence of any aldehyde. The aldehydes may, for example, be those having from 1 to 20 carbon atoms.

Accordingly, in a further embodiment, the present invention relates to a process as described above for reacting a composition I comprising at least one aldehyde with hydrogen in the presence of a catalyst in at least one main reactor and at least one postreactor, wherein the at least one aldehyde is selected from the group consisting of C1- to C20-aldehydes.

When composition I comprising at east one aldehyde comprises at least one organic compound, this composition I in the context of the present invention comprises in particular from 0.1 to 80% by weight, based on composition I, of the aldehyde. Composition I comprises preferably from 2 to 30% by weight, more preferably from 5 to 10% by weight of the aldehyde.

The process according to the invention is carried out in at least one main reactor and at least one postreactor. According to the invention, preferably at least 60% of composition I is reacted in the main reactor.

In the process according to the invention, at least 85% of composition I is more preferably reacted in the main reactor; particularly preferably, at least 90% of composition I is reacted in the main reactor.

Accordingly, the present invention relates, in a preferred embodiment, to a process as described above for reacting a composition I comprising at least one aldehyde with hydrogen in the presence of a catalyst in at least one main reactor and at least one postreactor, wherein at least 60% of composition I is reacted in the main reactor.

According to the invention, at least 50% of the fresh hydrogen fed to the reaction system is fed into at least one postreactor. In a more preferred embodiment, for example, at least 60% of the fresh hydrogen is fed into the postreactor, in particular at least 70%, even more preferably at least 80% and especially preferably at least 90%.

Accordingly, in the context of the present invention, especially from 60 to 100% of the fresh hydrogen fed to the reaction system is fed into at least one postreactor, preferably from 70 to 99%, more preferably from 80 to 95%.

The present invention relates accordingly, in a further embodiment, to a process as described above for reacting a composition I comprising at least one aldehyde with hydrogen in the presence of a catalyst in at least one main reactor and at least one postreactor, wherein at least 60% of the fresh hydrogen fed to the reaction system is fed into at least one postreactor.

According to the invention, it is likewise possible to feed further hydrogen to the reaction system, for example via at least one main reactor or a plurality of main reactors.

According to the invention, the offgas obtained in the process according to the invention can be discharged predominantly from or downstream of a main reactor. For instance, especially at least 70% of the offgas of the main reactor is discharged, preferably at least 75%, more preferably at least 80%, especially preferably at least 90%. Disregarding the dissolved portion of the hydrogen, preferably no gas passes from the main reactor(s) into the postreactor(s).

The present invention therefore relates, in a preferred embodiment, to a process as described above for reacting a composition I comprising at least one aldehyde with hydrogen in the presence of a catalyst in at least one main reactor and at least one postreactor, wherein at least 70% of the offgas of the main reactor is discharged.

It is equally possible in the context of the present invention that a portion of the offgas of the postreactor is discharged, especially when it is ensured that at least 50% of the hydrogen used in at least one main reactor stems from the offgas of the postreactor. In the context of the present invention, preferably at least 60% of the hydrogen used in at least one main reactor stems from the offgas of the postreactor, more preferably at least 70%, most preferably at least 80%.

Accordingly, the present invention also relates, in a preferred embodiment, to a process as described above for reacting a composition I comprising at least one aldehyde with hydrogen in the presence of a catalyst in at least one main reactor and at least one postreactor, wherein hydrogen passes from at least one main reactor to at least one postreactor only in the form of hydrogen dissolved in the product stream of the main reactor.

In the process according to the invention, the mixture obtained in the reaction in a main reactor is transferred into a further main reactor or a postreactor for further reaction. The product of the reaction of composition I with hydrogen is withdrawn from the postreactor in the present invention.

For the hydrogenation of composition I, it is possible to use any suitable catalysts. In particular, it is possible to use at least one homogeneous or at least one heterogeneous catalyst or both at least one homogeneous and at least one heterogeneous catalyst.

The usable catalysts preferably comprise at least one metal from transition group 7, 8, 9, 10 or 11 of the Periodic Table of the Elements. Preference is further given to the catalysts usable in accordance with the invention comprising at least one element selected from the group consisting of Re, Fe, Ru, Co, Rh, Ir, Ni, Pd, Pt, Cu and Au. Special preference is given to the catalysts usable in accordance with the invention comprising at least one element selected from the group consisting of Fe, Ni, Pd, Pt and Cu. Particular preference is given to the catalysts usable in accordance with the invention comprising Pd, Pt, Ru or Ni.

In a further embodiment, the present invention therefore relates to a process as described above for reacting a composition I comprising at least one aldehyde with hydrogen in the presence of a catalyst in at least one postreactor, wherein the catalyst comprises, as an active metal, Pd, Pt, Ru or Ni.

Homogeneous catalysts used with preference in the process according to the invention comprise at least one element of transition group 8, 9 or 10. Preference is further given to homogeneous catalysts which comprise Ru, Rh, Ir and/or Ni. Examples which should be mentioned in this context are $RhCl(TTP)_3$ or $Ru_4H_4(CO)_{12}$. Particular preference is given to those homogeneous catalysts which comprise Ru. For example, homogeneous catalysts used are those described in U.S. Pat. Nos. 5,180,870, 5,321,176, 5,177,278, 3,804,914, 5,210,349, 5,128,296, 316,917 and in D. R. Fahey in J. Org. Chem. 38 (1973) p. 80-87, whose disclosure-content on this subject is incorporated fully into the context of the present application. Such catalysts are, for instance, $(TPP)_2(CO)_3Ru$, $[Ru(CO)_4]_3$, $(TPP)_2Ru(CO)_2Cl_2$, $(TPP)_3(CO)RuH_2$, $(TPP)_2(CO)_2RuH_2$, $(TPP)_2(CO)_2RuClH$ or $(TPP)_3(CO)RuCl_2$.

Special preference is given in the context of the process according to the invention to using at least one heterogeneous catalyst, in which case it is possible to use at least one of the abovementioned metals in the form of the metal as such, in the form of Raney catalyst and/or applied to a customary support. Preferred support materials are, for instance, activated carbons or oxides, for example aluminas, silicas, titanias or zirconias. Other support materials which should be mentioned include bentonites. When two or more metals are used, they may be present separately or as an alloy. It is possible in this case to use at least one metal as such and at least one other metal in the form of Raney catalyst, or at least one metal as such and at least one other metal applied to at least one support, or at least one metal in the form of Raney catalyst and at least one other metal applied to at least one support, or at least one metal as such and at least one other metal in the form of Raney catalyst and at least one other metal applied to at least one support.

The catalysts used in the process according to the invention may, for example, also be what are known as precipitation catalysts. Such catalysts may be prepared by precipitating their catalytically active components from their salt solutions, in particular from the solutions of their nitrates and/or acetates, for example by adding solutions of alkali metal hydroxide and/or carbonate and/or alkaline earth metal hydroxide and/or carbonate solutions, for example sparingly soluble hydroxides, oxide hydrates, basic salts or carbonates, subsequently drying the resulting precipitates and then converting them by calcination at generally from 300 to 700° C., in particular from 400 to 600° C., to the corresponding oxides, mixed oxides and/or mixed-valence oxides, which are reduced by a treatment with hydrogen or with hydrogen-comprising gases in the range of generally 50-700° C., in particular from 100 to 400° C., to the metals and/or low-oxidation state oxidic compounds in question and converted to the actual catalytically active form. Reduction is generally effected until no more water is formed. In the preparation of precipitation catalysts which comprise a support material, the catalytically active components can be precipitated in the presence of the support material in question. The catalytically active components may advantageously be precipitated from the salt solutions in question simultaneously with the support material.

Preference is given to using hydrogenation catalysts in the process according to the invention which comprise the metals or metal compounds catalyzing the hydrogenation deposited on a support material.

Apart from the abovementioned precipitation catalysts which, apart from the catalytically active components, also additionally comprise a support material, support materials suitable for the process according to the invention are generally those in which the catalytically hydrogenating component has been applied to a support material, for example, by impregnation.

The way in which the catalytically active metal is applied to the support is generally not critical and can be brought about in various different ways. The catalytically active metals may be applied to these support materials, for example, by impregnation with solutions or suspensions of the salts or oxides of the elements in question, drying and subsequent reduction of the metal compounds to the metals or low-oxidation state compounds in question by means of a reducing agent, preferably with hydrogen or complex hydrides. Another means of applying the catalytically active metals to these supports is to impregnate the supports with solutions of thermally readily decomposable salts, for example with nitrates or thermally readily decomposable complexes, for example carbonyl or hydrido complexes of the catalytically active metals, and to heat the thus impregnated support to temperatures in the range from 300 to 600° C. to thermally decompose the adsorbed metal compounds. This thermal decomposition is preferably undertaken under a protective gas atmosphere. Suitable protective gases are, for example, nitrogen, carbon dioxide, hydrogen or the noble gases. In addition, the catalytically active metals may be deposited on the catalyst support by vapor deposition or by flame spraying. The content in these supported catalysts of the catalytically active metals is in principle not critical for the success of the process according to the invention. In general, higher contents of catalytically active metals in these supported catalysts lead to higher space-time conversions than lower contents. In general, supported catalysts are used whose content of catalytically active metals is in the range from 0.1 to 90% by weight, preferably in the range from 0.5 to 40% by weight, based on the total weight of the catalyst. Since these content data are based on the overall catalyst including support material, but the different support materials have very different specific weights and specific surface areas, it is also conceivable for the contents to be lower or higher than these data, without this having a disadvantageous effect on the result of the process according to the invention. It will be appreciated that a plurality of the catalytically active metals may also be applied to the particular support material. In addition, the catalytically active metals may also be applied to the support, for example, by the process of DE-A 25 19 817, EP 1 477 219 A1 or EP 0 285 420 A1. In the catalysts, according to the aforementioned documents, the catalytically active metals are present, in the form of an alloy which is; generated by thermal treatment and/or reduction of the, for example, by impregnation with a salt or complex of the aforementioned metals.

Both the precipitation catalysts and the supported catalysts may also be activated in situ at the start of the reaction by the hydrogen present. Preference is given to separately activating these catalysts before their use.

The support materials used may generally be the oxides of aluminum and of titanium, zirconium dioxide, silicon dioxide, aluminas, for example montmorillonites, silicates, for example magnesium silicates or aluminum silicates, zeolites, for example of the ZSM-5 or ZSM-10 structure types, or activated carbon. Preferred support materials are aluminas, titanium dioxides, silicon dioxide, zirconium dioxide and activated carbon. It will be appreciated that mixtures of different support materials may also serve as the support for catalysts usable in the process according to the invention.

According to the invention, very particularly preferred catalysts are those which comprise Ni, Pt and/or Pd and are applied to a support. Very preferred supports are or comprise activated carbon, aluminum oxide, titanium dioxide and/or silicon dioxide.

The same catalysts may be present in the main reactor(s) and postreactor(s), but this is not obligatory in the context of the present invention. It is also possible, for example, to use another catalyst in each of the reactors. For example, a suspension hydrogenation may be combined with homogeneous hydrogenation and/or heterogeneous hydrogenation. Particular preference is given to hydrogenation with heterogeneous catalysts, the catalyst used in the postreactor(s) in particular being used in the form of a fixed bed.

The at least one heterogeneous catalyst may be used, for example, in the form of a suspension catalyst and/or in the form of a fixed bed catalyst.

When, for example, in the process according to the invention, the hydrogenation is carried out with at least one suspension catalyst, hydrogenation is effected preferably in at least one stirred reactor or in at least one bubble column or in at least one packed bubble column or in a combination of two or more identical or different reactors.

The term "different reactors" refers in the present context both to different reactor types and to reactors of the same type which differ, for example, by their geometry, for example their volume and/or their cross section, and/or by the hydrogenation conditions in the reactors.

When, for example, in the process according to the invention, the hydrogenation is carried out with at least one fixed bed catalyst, preference is given to using at least one tubular reactor, for example at least one shaft reactor and/or at least one tube bundle reactor, and it is possible to operate a single reactor in liquid phase mode or trickle mode. When two or more reactors are used, it is possible to operate at least one in liquid phase mode and at least one in trickle mode.

In a preferred embodiment of the process according to the invention, the at least one catalyst used for the hydrogenation is removed from the product mixture of the hydrogenation after the reaction in a main reactor. Depending on the catalyst used, this removal can be effected in any suitable process.

A catalyst can likewise be removed downstream of a postreactor by a suitable process. The remarks which follow relate to the catalyst removal downstream of either a main reactor or a postreactor.

When the catalyst used in the hydrogenation is, for example, a heterogeneous catalyst as a suspension catalyst, preference is given in the context of the present invention to removing it by at least one filtration step. The catalyst removed in this way may be recycled into the hydrogenation or fed to at least one arbitrary other process. It is equally possible to work up the catalyst, in order, for example, to recover the metal present in the catalyst.

When the catalyst used in the hydrogenation is, for example, a homogeneous catalyst, preference is given to removing it in the context of the present invention by at least one distillation step. In this distillation, one or two or more distillation columns may be used. The catalyst removed in this way may be recycled into the hydrogenation or fed to at least one arbitrary other process. It is equally possible to work up the catalyst, in order, for example, to recover the metal present in the catalyst.

Before use in an arbitrary process, for example before recycling into the process according to the invention, either the at least one homogeneous or the at least one heterogeneous catalyst, can be regenerated, should this be necessary, by at least one suitable process.

The heat can be removed in the reactor used in accordance with the invention internally, for example via cooling coils, and/or externally, for example via at least one heat exchanger. When, for example and with preference, at least one tubular reactor is used for the hydrogenation, preference is given to conducting the reaction via external circulation, in which the heat removal is integrated.

When, in a preferred embodiment of the process according to the invention, the hydrogenation is carried out continuously, preference is further given to using at least two reactors, more preferably at least two tubular reactors, more preferably at least two serially coupled tubular reactors and especially preferably exactly two serially coupled tubular reactors. The hydrogenation conditions in each of the reactors used may be the same or different and are within the above-described ranges.

When the hydrogenation is carried out over at least one suspended catalyst, the residence time is generally in the range from 0.05 to 50 h, for example in the range from 0.5 to 50 h, preferably in the range from 1 to 30 h and more preferably in the range from 1.5 to 25 h, most preferably in the range from 1.5 to 10 h. It is unimportant whether, in accordance with the invention, one main reactor and one postreactor are used, or additionally further reactors. For all of these embodiments, the total residence time is within the above-specified ranges.

When, in the process according to the invention, the hydrogenation is carried out in continuous mode over at least one fixed bed catalyst, the catalyst hourly space velocity (kg of feed/liters of catalyst×h) is generally in the range from 0.03 to 20, preferably in the range from 0.05 to 5 and more preferably in the range from 0.1 to 2. It is unimportant whether, in accordance with the invention, one main reactor and one postreactor are used, or additionally further reactors. For all of these embodiments, the total hourly space velocity is within the above-specified ranges.

The postreactor(s) may be operated at the same temperature level as the main reactor, or at a lower or higher temperature level. In general, the hydrogenation temperature in the main reactor is in the range from 0 to 350° C., preferably in the range from 20 to 300° C., more preferably in the range from 50 to 250° C. and especially preferably in the range from 80 to 220° C.

The present invention therefore relates, in a further embodiment, to a process as described above for reacting a composition I comprising at least one aldehyde with hydrogen in the presence of a catalyst in at least one main reactor and at least one postreactor, wherein the reaction of composition I with hydrogen is carried out in the main reactor at a temperature in the range from 0 to 350° C.

The hydrogen pressure in the inventive hydrogenation in the main reactor is generally in the range from 1 to 325 bar, preferably in the range from 5 to 300 bar, more preferably in the range from 10 to 250 bar and especially preferably in the range from 15 to 150 bar. It is advantageous when the pressure level in the postreactor is equal to or higher than in the main reactor.

The present invention therefore relates, in a further embodiment, to a process as described above for reacting a composition I comprising at least one aldehyde with hydrogen in the presence of a catalyst in at least one main reactor and at least one postreactor, wherein the reaction of composition I with hydrogen in the main reactor is carried out at a pressure in the range from 1 bar to 325 bar.

The mixture which is obtained from the main reactor comprises reaction product, preferably converted organic compound, in a conversion, based on the overall mixture, preferably in the range from 60 to 99.9% and more preferably in the range from 70 to 99.5%. This mixture is, if appropriate after at least one suitable intermediate treatment, fed to the postreactor. The mixture which is obtained from the postreactor comprises reaction product, preferably converted organic compound, in a fraction preferably in the range of at least 99.5%, more preferably in the range of 99.9% and especially preferably of 99.99%.

In the inventive hydrogenation, at least one suitable solvent or diluent may be used. In principle, these include all solvents and diluents which are not hydrogenated or converted in another way under the hydrogenation conditions, for example alcohols, ethers, hydrocarbons, water, aromatics or ketones. When cyclododecadienone is present in composition I as an organic compound, especially suitable solvents include toluene or cyclododecane.

In a preferred embodiment of the process according to the invention, the hydrogenation is carried out without addition of a solvent or diluent.

The inventive hydrogenation generally affords a mixture which, in addition to reaction product, preferably comprises converted organic compound, with or without at least one by-product and/or at least one further compound which has been fed to the hydrogenation via, for example, a mixture comprising the organic compound. From this mixture, the reaction product, preferably converted organic compound, may be removed by means of at least one suitable method, for example and with preference via at least one distillation.

The process according to the invention features a high conversion, which leads to a high purity of the resulting products. The catalyst lifetime, in particular in the main reactor, increases; the catalyst activity in the postreactor is higher as a result of the smaller amounts of CO, i.e. less catalyst can be used in accordance with the invention, and generally less reaction pressure also has to be applied.

The present invention is illustrated by the examples which follow.

EXAMPLES

Comparative Example 1

Hydrogenation of cyclododeca-4,8-dien-1-one to cyclododecanone

In a reactor battery consisting of a tubular reactor with liquid circuit and a postreactor, cyclododeca-4,8-dien-1-one was hydrogenated continuously (30 bar, temperatures 130°, each reactor in trickle mode, catalyst 0.2% Pd on alumina), which also comprised approx. 0.5% polyunsaturated C12-aldehydes. The entire amount of hydrogen (2.1 molar equivalents based on reactant, i.e. 5 mol % hydrogen excess) was introduced into the main reactor and transferred together with the product stream into the postreactor. Downstream of the postreactor, the residual gas was discharged as offgas. At a total catalyst hourly space velocity of 0.5 kg of dienone/liter of catalyst×h, the conversion was 99.8%, i.e. the reaction effluent still contained 0.2% of unconverted olefin. In a subsequent distillation, it was possible to obtain cyclododecanone in a purity of 99.4%; 0.2% of unsaturated cyclododecanone was undesired secondary constituent.

Example 1

Hydrogenation of cyclododeca-4,8-dien-1-one to cyclododecanone

Comparative Example 1 was repeated with the difference that the hydrogen was introduced into the postreactor and the remaining hydrogen was transferred therefrom into the main reactor, from which the offgas was discharged. The conversion downstream of the postreactor was 99.99%. The distillation afforded cyclododecanone in a purity of 99.6%. Undesired unsaturated products were present only with a content of 100 ppm.

Comparative Example 2

Hydrogenation of Dehydrolysmeral to Lysmeral

Analogously to Comparative Example 1, a mixture of 50% methanol, 29% dehydrolysmeral, 13% tert-butylbenzaldehyde, 5% water and 3% other components such as propanol, propanal, various esters and high boilers such as sodium salts was hydrogenated. The catalyst used was 5% Pd on activated carbon. The hydrogenation temperature in the main reactor was approx. 80° C., in the postreactor approx. 130° C.; the reaction pressure was 15 bar. The hydrogen excess based on dehydrolysmeral was 1.05 molar equivalents. The dehydrolysmeral conversion at a catalyst hourly space velocity of approx 2 kg/liter of catalyst×h was 93% downstream of the postreactor and the lysmeral selectivity was 91%.

Example 2

Comparative Example 2 was repeated analogously to Example 1. The conversion downstream of the postreactor was 97% and the lysmeral selectivity was 94%

What is claimed is:

1. A process for reacting a composition I, comprising cyclododeca-4,8-dien-1-one obtained by reacting 1,5,9-cyclododecatriene with dinitrogen monoxide and further comprising polyunsaturated C12 aldehydes as a result of the preparation process of the cyclododeca-4,8-dien-1-one, with hydrogen in the presence of a heterogeneous Pd catalyst in a main reactor and a postreactor to afford a mixture comprising cyclododecanone, and removing the cyclododecanone from this mixture via at least one distillation;
   wherein at least 50% of the fresh hydrogen fed to the reaction system is fed into the postreactor; and
   wherein in the preparation process of the cyclododeca-4,8-dien-1-one, 1,5,9-cyclododecatriene is reacted in continuous mode with dinitrogen monoxide in a single reactor at a temperature in the range from 200 to 300° C., a pressure in the range from 50 to 200 bar and a residence time of the reactants in the range from 0.25 to 10 h, wherein in the feed which is fed to the reaction of dinitrogen monoxide with the 1,5,9-cyclododecatriene, the molar ratio of dinitrogen monoxide to 1,5,9-cyclododecatriene is in the range from 0.1 to 0.4.

2. The process as claimed in claim 1, wherein more than 50% of the hydrogen used in at least one main reactor stems from the offgas of the postreactor.

3. The process according to claim 1, wherein hydrogen is used in an excess of from 0.1 to 50 mol %.

4. The process according to claim 1, wherein at least 60% of composition I is reacted in the main reactor.

5. The process according to claim 2, wherein at least 60% of composition I is reacted in the main reactor.

6. The process according to claim 1, wherein at least 60% of the fresh hydrogen fed to the reaction system is fed into at least one postreactor.

7. The process according to claim 2, wherein at least 60% of the fresh hydrogen fed to the reaction system is fed into at least one postreactor.

8. The process according to claim 1, wherein at least 70% of the offgas of the main reactor is discharged.

9. The process according to claim 8, wherein hydrogen passes from at least one main reactor to at least one postreactor only in the form of hydrogen dissolved in the product stream of the main reactor.

10. The process according to claim 1, wherein the reaction of composition I with hydrogen in the main reactor is carried out at a temperature in the range from 0° C. to 350° C.

11. The process according to claim 1, wherein the reaction of composition I with hydrogen in the main reactor is carried out at a pressure in the range from 1 bar to 325 bar.

12. A process for reacting a composition I, comprising cyclododeca-4,8-dien-1-one obtained by reacting 1,5,9-cyclododecatriene with dinitrogen monoxide and further comprising polyunsaturated C12 aldehydes as a result of the preparation process of the cyclododeca-4,8-dien-1-one, with hydrogen in the presence of a heterogenous Pd catalyst in a main reactor and a postreactor to afford a mixture comprising cyclododecanone, and removing the cyclododecanone from this mixture via at least one distillation;
  wherein at least 50% of the fresh hydrogen fed to the reaction system is fed into the postreactor;
  wherein more than 50% of the hydrogen used in the main reactor stems from the offgas of the postreactor;
  wherein in the preparation process of the cyclododeca-4,8-dien-1-one, 1,5,9-cyclododecatriene is reacted in continuous mode with dinitrogen monoxide in a single reactor at a temperature in the range from 200 to 300° C., a pressure in the range from 50 to 200 bar and a residence time of the reactants in the range from 0.25 to 10 h, wherein the feed which is fed to the reaction of dinitrogen monoxide with the 1,5,9-cyclododecatriene, the molar ratio of dinitrogen monoxide to 1,5,9-cyclododecatriene is in the range from 0.1 to 0.4.

13. A process for reacting a composition I, comprising cyclododeca-4, 8-dien-1-one obtained by reacting 1,5,9-cyclododecatriene with dinitrogen monoxide and further comprising polyunsaturated C12 aldehydes as a result of the preparation process of the cyclododeca-4,8-dien-1-one, with hydrogen in the presence of a heterogeneous Pd catalyst in a main reactor and a postreactor to afford a mixture comprising cyclododecanone, and removing the cyclododecanone from this mixture via at least one distillation;
  wherein at least 50% of the fresh hydrogen fed to the reaction system is fed into the postreactor;
  wherein more than 50% of the hydrogen used in the main reactor stems from the offgas of the postreactor;
  wherein at least 60% of composition I is reacted in the main reactor; and
  wherein in the preparation process of the cyclododeca-4,8-dien-1-one, 1,5,9-cyclododecatriene is reacted in continuous mode with dinitrogen monoxide in a single reactor at a temperature in the range from 200 to 300° C., a pressure in the range from 50 to 200 bar and a residence time of the reactants in the range from 0.25 to 10 h, wherein in the feed which is fed to the reaction of dinitrogen monoxide with the 1,5,9-cyclododecatriene, the molar ratio of dinitrogen monoxide to 1,5,9-cyclododecatriene is in the range from 0.1 to 0.4.

14. A process for reacting a composition I, comprising cyclododeca-4,8-dien-1-one obtained by reacting 1,5,9-cyclododecatriene with dinitrogen monoxide and further comprising polyunsaturated C12 aldehydes as a result of the preparation process of the cyclododeca-4,8-dien-1-one, with hydrogen in the presence of a heterogeneous Pd catalyst in a main reactor and a postreactor to afford a mixture comprising cyclododecanone, and removing the cyclododecanone from this mixture via at least one distillation;
  wherein at least 50% of the fresh hydrogen fed to the reaction system is fed into the postreactor;
  wherein more than 50% of the hydrogen used in the main reactor stems from the offgas of the postreactor;
  wherein at least 60% of the fresh hydrogen fed to the reaction system is fed into; and
  wherein in the preparation process of the cyclododeca-4,8-dien-1-one, 1,5,9-cyclododecatriene is reacted in continuous mode with dinitrogen monoxide in a single reactor at a temperature in the range from 200 to 300° C., a pressure in the range from 50 to 200 bar and a residence time of the reactants in the range from 0.25 to 10 h, wherein in the feed which is fed to the reaction of dinitrogen monoxide with the 1,5,9-cyclododecatriene, the molar ratio of dinitrogen monoxide to 1,5,9-cyclododecatriene is in the range from 0.1 to 0.4.

15. A process for reacting a composition I, comprising cyclododeca-4,8-dien-1-one obtained by reacting 1,5,9-cyclododecatriene with dinitrogen monoxide and further comprising polyunsaturated C12 aldehydes as a result of the preparation process of the cyclododeca-4,8-dien-1-one, with hydrogen in the presence of a heterogeneous Pd catalyst in a main reactor and a postreactor to afford a mixture comprising cyclododecanone, and removing the cyclododecanone from this mixture via at least one distillation;
  wherein at least 50% of the fresh hydrogen fed to the reaction system is fed into the postreactor;
  wherein more than 50% of the hydrogen used in the main reactor stems from the offgas of the postreactor;
  wherein at least 60% of composition I is reacted in the main reactor;
  wherein at least 70% of the offgas of the main reactor is discharged; and
  wherein in the preparation process of the cyclododeca-4,8-dien-1-one, 1,5,9-cyclododecatriene is reacted in continuous mode with dinitrogen monoxide in a single reactor at a temperature in the range from 200 to 300° C., a pressure in the range from 50 to 200 bar and a residence time of the reactants in the range from 0.25 to 10 h, wherein in the feed which is fed to the reaction of dinitrogen monoxide with the 1,5,9-cyclododecatriene, the molar ratio of dinitrogen monoxide to 1,5,9-cyclododecatriene is in the range from 0.1 to 0.4.

16. The process as claimed in claim 14 wherein at least 60% of the fresh hydrogen fed to the reaction system is fed into the postreactor.

17. The process as claimed in claim 15 wherein at least 60% of the fresh hydrogen fed to the reaction system is fed into the postreactor.

* * * * *